United States Patent [19]

Stuitje

[11] 4,161,875
[45] Jul. 24, 1979

[54] APPARATUS FOR MEASURING THE ALCOHOL PERCENTAGE IN THE BREATH OF AN EXAMINEE

[75] Inventor: Cornelis C. Stuitje, Zeist, Netherlands

[73] Assignee: Detecta-Kraan B.V., Zeist, Netherlands

[21] Appl. No.: 867,514

[22] Filed: Jan. 6, 1978

[30] Foreign Application Priority Data

Jan. 20, 1977 [NL] Netherlands ............................ 770054

[51] Int. Cl.² .............................................. G01N 31/00
[52] U.S. Cl. ............................................. 73/23; 422/84
[58] Field of Search ............... 73/23, 27 R; 23/254 E, 23/255 E; 128/2 C; 340/632–634; 422/84, 94–98

[56] References Cited

U.S. PATENT DOCUMENTS

| | | | |
|---|---|---|---|
| 3,075,379 | 1/1963 | Schmauch | 73/27 R |
| 3,238,783 | 3/1966 | Wright | 128/2 C X |
| 3,854,320 | 12/1974 | Burroughs et al. | 73/23 |
| 3,858,434 | 1/1975 | Hoppesch et al. | 23/254 E |
| 3,877,291 | 4/1975 | Hoppesch et al. | 73/27 R |

Primary Examiner—James J. Gill
Attorney, Agent, or Firm—Lane, Aitken & Ziems

[57] ABSTRACT

Apparatus for measuring the alcohol percentage in the breath of a person by blowing the breath into an airtight chamber enclosing a gas detector of the type of which the electric resistance changes upon exposure to alcohol vapor. The breath is introduced into the chamber in such manner that it does not directly strike the gas detector, so that a cooling of the gas detector by the air flow is avoided. Thus, the resistance change of the gas detector is substantially exclusively dependent on the alcohol percentage in the breath, whereby a very accurate measurement is obtained.

13 Claims, 2 Drawing Figures

APPARATUS FOR MEASURING THE ALCOHOL PERCENTAGE IN THE BREATH OF AN EXAMINEE

BACKGROUND OF THE INVENTION

The invention relates to an apparatus for measuring the alcohol percentage in the breath of an examinee, in particular to establish whether the examinee is fit to drive a motor car.

It is known to measure this alcohol percentage by means of a blow pipe, which contains certain crystals of which the color changes when the alcohol percentage of the breath blown into the blow pipe exceeds a predetermined limit. However, this blow pipe has the disadvantage that the measurement is rather inaccurate.

Furthermore, there has been disclosed a gas indicator containing a gas detector of which the electric resistance changes upon exposure to a gas. The gas detector may comprise a body of a semi-conductive material, in particular a metal oxide of the N-type, such as tin oxide, zinc oxide, or ferric sesquioxide. Two spaced electrodes are incorporated in the body, and one of these electrodes serves as a filament for heating the body. The resistance of the gas detector, which is low in its cold condition, is considerably increased by the heating. When the hot gas detector is exposed to a gas, the resistance decreases again in dependence on the concentration of the gas. The gas detector may be responsive, inter alia, to hydrogen, carbon monoxide, methane, propane or alcohol vapor.

The above-mentioned gas indicator is intended to measure relatively large gas concentrations in an open space. In such a measurement, slight variations of the resistance of the gas detector have no influence on the results. Slight resistance variations of this kind may be due, for instance, to an air current along the detector, causing a slight cooling of the body, whereby the resistance is somewhat decreased.

If a gas indicator of this kind is used to measure the alcohol percentage in the breath of a person by blowing the breath onto the gas detector, the latter is cooled by the air flow, so that the resistance is not only decreased by the alcohol percentage, if any, but also by the cooling. For the small percentages to be measured in such a case (0.05–0.08%), this effect has a considerable influence, so that a reliable measurement by means of the gas indicator is not possible.

SHORT SUMMARY OF THE INVENTION

It is the main object of the invention to provide a measuring apparatus comprising a gas detector of the above-mentioned kind, which allows for an accurate measurement of the alcohol percentage in the breath of a person.

It is a further object of the invention to provide such an apparatus wherein a cooling of the gas detector by an air flow is avoided, so that the resistance of the gas detector is substantially exclusively dependent on the alcohol percentage.

According to the invention, the apparatus comprises an airtight chamber provided with a gas inlet channel for blowing the breath into the chamber, and with an air outlet channel including a check valve, and enclosing a gas detector of which the electric resistance is influenced by the alcohol vapor, the position of the gas detector in the chamber, the direction of the air inlet channel, and the place where the air inlet channel opens into the chamber being chosen in such manner that the breath blown into the chamber does not immediately strike the gas detector.

SHORT DESCRIPTION OF THE DRAWINGS

DETAILED DESCRIPTION

Figure 1:
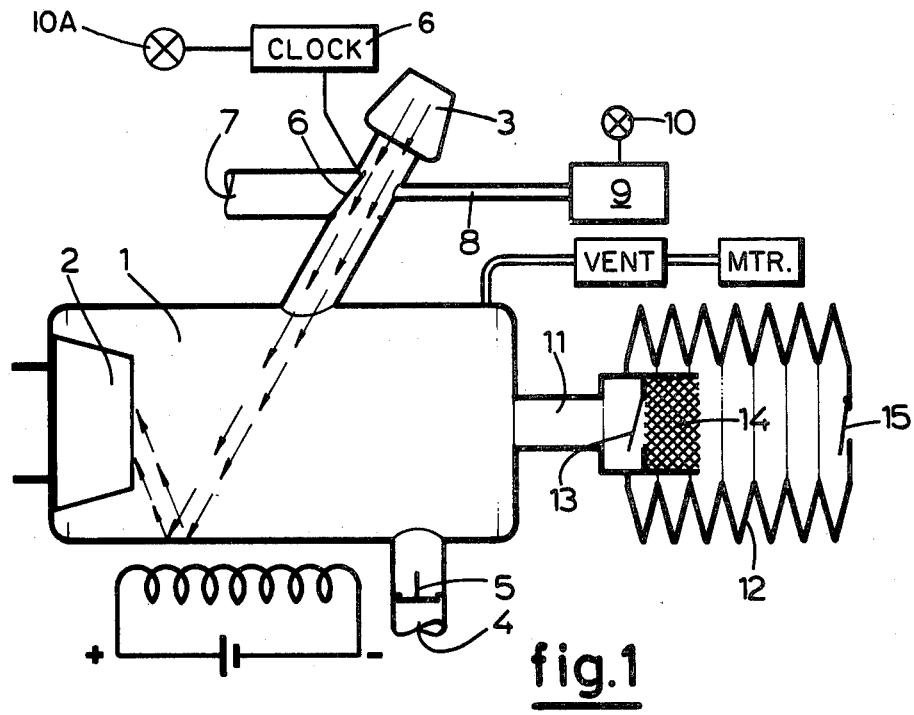
FIG. 1 shows a cross section of the chamber enclosing the gas detector in an apparatus according to the invention.

The measuring apparatus shown in FIG. 1 comprises a cylindrical chamber 1, enclosing a gas detector 2 attached to one of the end walls of the chamber. The chamber 1 is provided with an air inlet channel 3 for blowing in the breath, which is inclined with respect to the axis of the chamber 1 in such manner that the air flow cannot directly strike the gas detector 2. In addition, an air outlet channel 4 has been provided near the other end wall of the chamber 1, opposite to the gas detector 2, so that the air flows away from the gas detector. As a consequence, the chamber 1 is saturated with the supplied breath, but the air flow does not immediately reach the gas detector, so that the gas detector only responds to the alcohol percentage. The air blown into the chamber 1 is discharged through the outlet channel 4. This channel comprises a check valve 5, so that no air can flow into the chamber 1 through the channel 4.

The air inlet channel 3 is provided with an inlet valve 6 closing the entry to the chamber 1 in its rest position. In this situation, the air supplied to the air inlet channel 3 is discharged through an auxiliary outlet 7. When the inlet valve is brought into its operative position, the auxiliary outlet 7 is closed off, so that the air supplied to the air inlet channel 3 flows into the chamber 1. Furthermore, the air inlet channel 3 is provided with a branch channel 8 connected with a pressure switch 9. The branch channel 8 is connected with the air inlet channel 3 in such manner that the pressure switch is actuated whenever air is blown in, both in the rest position and in the operative position of the inlet valve 6. The pressure switch actuates a signal lamp 10 serving to check whether the person to be examined blows continuously. As shown in FIG. 1, an electronic clock C is connected to and started by the inlet valve 6 and actuates another signal lamp 10A at the end of a predetermined time interval after the air inlet channel 3 is connected with the chamber 1.

The chamber 1 is provided with an additional inlet channel 11, serving as a scavenging channel, and connected with a bellows 12, including a check valve 13, an air filter 14, and an inlet valve 15. After the end of a measurement, the chamber 1 may be scavenged with fresh air by means of the bellows 12. It is also possible, for this purpose, to use a ventilator connected with the scavenging channel and driven by a motor, as shown in FIG. 1.

Finally, the chamber 1 is provided with a heating coil to keep it at a constant temperature. The heating also has the effect that only the alcohol vapor participates in the measurements, and that other gases in the breath only have a slight influence.

Figure 2:
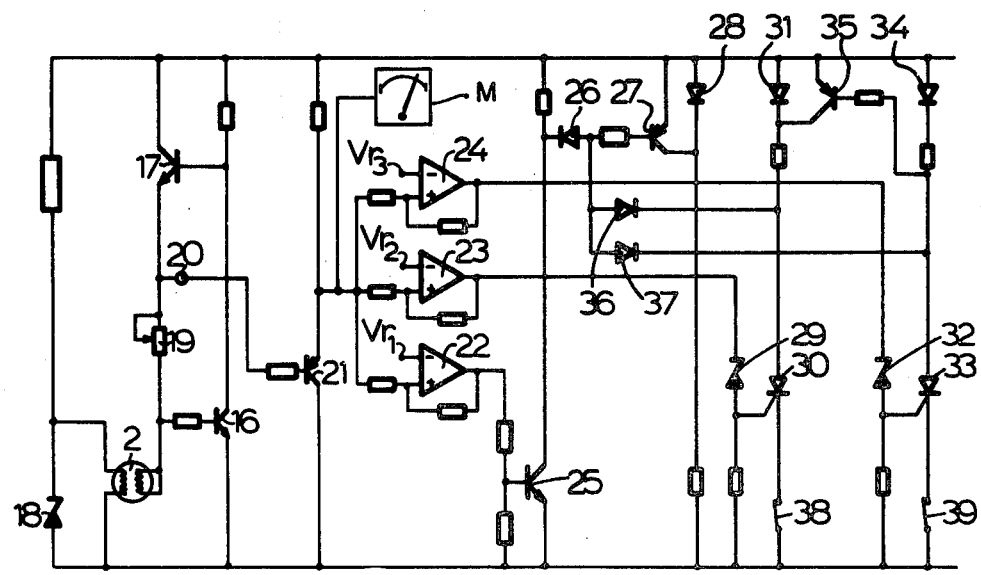
FIG. 2 shows the electric circuit diagram of an apparatus according to the invention.

As shown in FIG. 2, the heating filament of the gas detector 2 is connected with a Zener diode 18 in order to obtain a suitable operating voltage which is not very sensitive to variations of the feed voltage. The measuring electrode of the detector 2 is connected through a resistor with the base of a transistor 16. The collector of the transistor 16 is connected with the base of a transistor 17, of which the emitter is connected with a terminal 20. The terminal 20 is connected through an adjustable resistor 19 with the measuring electrode of the gas detector 2. As a consequence, the voltage at the terminal 20 is increased when the resistance of the gas detector is decreased. The voltage variation for a given variation of the resistance of the gas detector may be adjusted by means of the resistor 19.

The terminal 20 is connected through a resistor with the base of a transistor 21. The emitter of the transistor 21 is coupled with three operational amplifiers 22, 23 and 24. The inverting inputs of these amplifiers are connected with adjustable reference voltages $Vr_1$, $Vr_2$ and $Vr_3$, respectively. The non-inverting inputs are each connected through a resistor with the emitter of the transistor 21. The output of each amplifier is connected through a resistor with its non-inverting input, so that a slight positive feed-back is obtained, which allows for a rapid change-over. The reference voltages are adjusted in such manner that the output voltages of the amplifiers are low when the resistance of the detector has a high value.

The output of the amplifier 22 is connected through a voltage divider with the base of a transistor 25 of which the collector controls a transistor 27 through a diode 26. If the output voltage of the amplifier 22 is low, the transistor 27 is blocked and the light emitting diode 28 is ignited. The diode 28 indicates that the circuit is ready for a measurement. The diode 28 is extinguished at an alcohol percentage which may be adjusted by means of the voltage $Vr_1$. If the diode 28 remains conductive, this means that the person examined did not drink any alcohol.

The output of the amplifier 23 is connected through a Zener diode 29 with the control electrode of a thyristor 30. When the alcohol percentage exceeds a limit value adjusted by means of the voltage $Vr_2$ (for instance 0.05%), the amplifier 23 is changed over, so that the thyristor 30 and the light emitting diode 31 are ignited.

The output of the amplifier 24 controls a thyristor 33 in the same manner, through a Zener diode 32. When the amplifier 24 is changed over at a limit value adjusted by means of the voltage $Vr_3$ (for instance 0.08%), a light emitting diode 34 is ignited; at the same time, a transistor 35 is rendered conductive, whereby the light emitting diode 31 is extinguished.

Whenever one of the diodes 31 and 34 is ignited, the transistor 27 is rendered conductive through one of the diodes 36 and 37, whereby the light emitting diode 28 is extinguished.

Instead of the above-mentioned light emitting diodes, other means may be used to indicate the alcohol percentage, for instance, a moving coil instrument M calibrated in percents and connected to the emitter of transistor 21, as shown in FIG. 1.

After the measurement has been terminated and the chamber scavenged, a resetting key may be actuated to energize a relay having break contacts 38 and 39, whereby the ignited light emitting diode 31 or 34 is extinguished. Upon release of the resetting key, the relay is de-energized, so that the contacts 38 and 39 are closed. However, the diodes 31 and 34 remain in the extinguished condition, since the output voltages of the amplifiers 23 and 24 are low. The diode 28 is reignited to indicate that a new measurement may be performed.

During a measurement, the person to be examined must blow for about 15 seconds. During the first 5 seconds, the air blown into the air inlet channel 3 is discharged through the auxiliary outlet 7 in order to eliminate the gases occurring in the mouth, so that only air from the lower parts of the lungs is used for the measurement. This leads to a better agreement with the alcohol percentage of the blood. After the above-mentioned 5 seconds, a start key is actuated, whereby the inlet valve 6 is changed over, and the auxiliary outlet is closed, so that the air is directed to the chamber 1. By means of the signal lamp 10, a check is made whether the person to be examined blows continuously. Otherwise, the person to be examined might inhale fresh air to influence the measurement.

Upon actuation of the start key, a timing member is started, which ignites a signal lamp after 10 seconds to indicate that the measuring interval is terminated. After release of the start key, the alcohol percentage is determined by means of the light emitting diodes 28, 31 and 34, which may emit green, yellow and red light, respectively. Three different situations may occur, namely:

(1) The green diode 28 is ignited, which means that the person to be examined has not drunk any alcohol, or only a small quantity.

(2) The yellow diode 31 is ignited, which means that the alcohol percentage in the breath of the person is 0.05 to 0.08%.

(3) The red diode 34 is ignited, which means that the alcohol percentage in the breath of the person is above 0.08%.

After the chamber 1 has been scavenged by means of the bellows 12, the resetting key is actuated. After a short waiting time (for instance two minutes), in which the chamber and the detector regain the right temperature, the apparatus is again ready for use.

It is possible to provide a circuit indicating by means of a signal lamp whether the feed voltage has been temporarily interrupted. In such a case, the apparatus is released for measurement after some time (for instance one minute) to prevent the results from being influenced by a temperature decrease of the detector and the chamber.

The invention is not restricted to the above-described embodiment which may be modified in various manners within the scope of the invention.

For instance, it is possible to provide an electronic control circuit, actuated by a switch closed upon a supply of air to the air inlet channel, which performs the above-described operations automatically and prevents measuring errors by suitable security devices.

I claim:

1. Apparatus for measuring the alcohol percentage in the breath of an examinee, comprising an air-tight chamber, inlet and outlet openings in the chamber, an air inlet channel connected with said inlet opening for blowing the breath into the same, an air outlet channel connected with said outlet opening, a check valve arranged in said air outlet channel, a gas detector enclosed by said chamber of which the electric resistance is influenced by alcohol vapor and means responsive to the electric resistance of said gas detector for indicating the alcohol percentage, said gas detector being positioned in the chamber and exposed at all times to the interior of the chamber, the air inlet channel and opening being positioned so that breath blown into the chamber will deflect off of at least one of the inner walls of the chamber before coming in contact with the gas detector.

2. Apparatus as claimed in claim 1, wherein said gas detector comprises a semi-conductive body, and two spaced electrodes incorporated in said body, means being provided to supply a heating current to one of the said electrodes for heating said body, whereby it is activated and acquires the property that its electric resistance is considerably decreased upon exposure to alcohol vapor.

3. Apparatus as claimed in claim 1, wherein said chamber has a cylindrical shape and is provided with a first and a second end wall opposite to each other and perpendicular to the axis of said chamber, said gas detector being arranged on said first end wall, and said air inlet channel being inclined with respect to the axis of said chamber so as to include an obtuse angle with said axis as seen from said gas detector.

4. Apparatus as claimed in claim 3, wherein said air outlet channel is arranged near the second end wall of said chamber.

5. Apparatus as claimed in claim 1, further comprising a scavenging channel connected with said chamber, and means for supplying fresh air to said scavenging channel.

6. Apparatus as claimed in claim 5, wherein said fresh air supplying means include a bellows, a check valve within said bellows, and an air filter within said bellows.

7. Apparatus as claimed in claim 5, wherein said fresh air supplying means include a ventilator, and a motor for driving said ventilator.

8. Apparatus as claimed in claim 1, further comprising means for heating said chamber.

9. Apparatus as claimed in claim 1, further comprising a branch channel connected with said air inlet channel, a pressure switch connected with said branch channel, and a signal lamp actuated by said pressure switch.

10. Apparatus as claimed in claim 1, further comprising an auxiliary air outlet channel, and a valve in said air inlet channel connecting said air inlet channel with said auxiliary outlet channel in a first position, and with said chamber in a second position.

11. Apparatus as claimed in claim 1, wherein the said indicating means comprise an electronic switching circuit responsive to the electric resistance of said gas detector, and a plurality of optical indicators controlled by said switching circuit and each indicating an associated range of the alcohol percentage.

12. Apparatus as claimed in claim 1, wherein the said indicating means comprise an indicator responsive to the electric resistance of said gas detector and providing a continuous indication of the alcohol percentage.

13. Apparatus as claimed in claim 10, further comprising an electronic clock delivering a signal at the end of a predetermined time interval, and means for starting said clock when said air inlet channel is connected with said chamber.

* * * * *